United States Patent [19]

Chu

[11] 3,963,805

[45] June 15, 1976

[54] WATER SWELLABLE POLY(ALKYLENE OXIDE)

[75] Inventor: Nan S. Chu, Hartsdale, N.Y.

[73] Assignee: Union Carbide Corporation, New York, N.Y.

[22] Filed: Oct. 30, 1974

[21] Appl. No.: 519,268

[52] U.S. Cl. .............................. 260/874; 260/2 A; 260/2 BP
[51] Int. Cl.² ........................................ C08L 71/02
[58] Field of Search ................. 260/2 A, 2 BP, 874

[56] References Cited

UNITED STATES PATENTS

| | | | |
|---|---|---|---|
| 3,033,841 | 5/1962 | Germain | 260/874 |
| 3,281,499 | 10/1966 | Dolce et al. | 260/874 |
| 3,627,839 | 12/1971 | Vandenberg | 260/874 |
| 3,763,277 | 10/1973 | Chu et al. | 260/874 |

FOREIGN PATENTS OR APPLICATIONS 1,302,320   1962   France .............................. 260/2 A

*Primary Examiner*—H.S. Cockeram
*Attorney, Agent, or Firm*—Clement J. Vicari

[57] ABSTRACT

A process for producing water swellable poly(alkylene oxide) which comprises introducing into a reaction zone an admixture of poly(alkylene oxide) having a molecular weight of at least 100,000 and an inert hydrocarbon solvent containing a free radical catalyst; adding to said reaction zone acrylic acid, heating said reaction zone at a temperature within the range of about 40°C to about 100°C for a time sufficient to produce said water swellable poly(alkylene oxide), and thereafter recovering said water swellable poly(alkylene oxide) from said reaction zone.

8 Claims, No Drawings

WATER SWELLABLE POLY(ALKYLENE OXIDE)

The present invention relates to water swellable poly(alkylene oxide) and more particularly to a process for producing cross-linked poly(ethylene oxide) having a relatively high degree of water-pickup ability and stability.

The use of various materials as absorbents for moisture is a well known wide spread practice. Within the past few years recent innovations have resulted in the production of materials having irreversible absorption properties, i.e., the absorbed moisture is retained in the absorbent material under an applied pressure. These materials are now known as hydrogels and have particular utility in surgical dressings, diapers, bed pads, catamenial devices and the like. In most instances hydrogels have been produced in powder or particulate form and even, in some instances in film form. An especially interesting characteristic of the hydrogel polymers is that when in contact with water they absorb it and swell to a certain point and stop, and the final swollen polymer is still similar in shape to its initial unswollen shape. Many of the hydrogels have the ability to absorb many times their original weight in water without becoming soggy or deformed. Among the U.S. patents that have issued in this field are U.S. Pat. Nos. 3,669,103; 3,264,202; and 3,419,006. This is but an exemplary listing and should not be considered complete.

As will be evident from a reading of the above patents, cross-linked poly(alkylene oxide) and particularly cross-linked poly(ethylene oxide) are especially suitable hydrogel materials.

It is known that poly(alkylene oxide) such as poly(ethylene oxide) can be cross-linked readily through irradiation with gamma rays. Poly(ethylene oxide) has been shown to form a cross-linked polymer of varying properties through irradiation with gamma rays such as those emitted by a cobalt 60 source. The properties of these irradiated poly(ethylene oxides) are highly dependent on the irradiation dose, that is, the irradiated poly(ethylene oxide) may range in properties from a soluble polymer with properties similar to the unirradiated polymer, to a highly cross-linked horny solid, insoluble in any solvent. Unfortunately, gamma radiation involves the use of a potentially dangerous source with costly protective measures involved in its use, and therefore, this route is not the most desirable process for cross-linking poly(ethylene oxide).

In order to eliminate some of the disadvantages of obtaining cross-linked poly(alkylene oxide), via irradiation, it has been proposed to chemically crosslink poly(alkylene oxide) utilizing a di-vinyl monomer in the presence of a free radical catalyst (Canadian Pat. No. 756,190).

Unfortunately, however, this known chemical technique is not entirely satisfactory from a practical commercial standpoint, because the highest degree of cross-linking is obtained by employment of poly(alkylene oxide) in molten form. The utilization of poly(alkylene oxide) in molten form is difficult to process, whereas high concentrations of poly(alkylene oxide) in solution are extremely viscous and consequently also difficult to handle.

Water swellable poly(ethylene oxide) can also be obtained by heating a mixture of poly(ethylene oxide) with a free radical initiator and a bi- or polyfunctional monomer such as a diacrylate or methylene-bis-acrylamide. Unfortunately however, because of the susceptibility of the diacrylate or methylene bis-acryl amide toward hydrolysis, the di-or polyacrylate cross-linked poly (ethylene oxide) is not entirely satisfactory for certain uses where long term stability of the swollen polymer is important. This is attributable to the fact that once hydrolysis occurs, the cross-linkages would not be there and the swollen polymer would thus become soluble.

As far as I am aware, prior to the invention contemplated herein, water swellable poly(ethylene oxide) can only be obtained by the above described techniques, i.e. by radiation treatment or by the utilization of bi- or polyfunctional cross-linking agents.

I have found that water swellable poly(ethylene oxide) can also be produced by heating a mixture of poly (ethylene oxide) with acrylic acid (a monofunctional compound) and a free radical initiator such as acetyl peroxide in a hydrocarbon solvent. Although no bi- or polyfunctional monomer is utilized, the resultant product behaves as if it were cross-linked. Although the exact nature of the cross-linkage is not known, it has been found that the cross-linked polymer swells in water but does not dissolve in water.

Accordingly, in a broad aspect, the present invention contemplates the production of water swellable poly(alkylene oxide) by a process which comprises introducing into a reaction zone an admixture of poly(alkylene oxide), having a molecular weight of at least 100,000 and an inert hydrocarbon solvent containing a free radical catalyst; adding to said reaction zone acrylic acid, heating said reaction zone at a temperature within the range of 50°C to about 100°C for a time sufficient to produce said water swellable poly(alkylene oxide), and thereafter recovering said water swellable poly(alkylene oxide) from said reaction zone.

In a more specific aspect, the invention is utilized for producing water swellable poly(ethylene oxide) by the process which comprises introducing into a reaction zone an admixture of poly(ethylene oxide) having a molecular weight of at least 100,000 and an inert hydrocarbon solvent preferably an aliphatic hydrocarbon solvent containing a free radical catalyst preferably acetyl peroxide, continuously adding acrylic acid to the admixture of poly(ethylene oxide), solvent and catalyst in the reaction zone while maintaining the temperature of the reaction zone within the range of about 40°C to about 100°C preferably from about 50°C to about 80°C, said acrylic acid being added continuously in an amount sufficient to produce said water swellable poly(ethylene oxide).

I have found that the manner of mixing the reactants is critical. Water swellable alkylene oxide such as poly(ethylene oxide) is obtained only when acrylic acid is added to the reaction mixture and when the poly(alkylene oxide) is present in this mixture during the addition. Soluble poly(alkylene oxide) is recovered when poly(ethylene oxide) is added to the mixture after the addition of all the acrylic acid.

In a preferred technique a suspension of poly(ethylene oxide), i.e., poly(ethylene oxide) dispersed in an inert hydrocarbon such as an aliphatic hydrocarbon solvent, is added to a reaction zone together with a portion of acrylic acid solution (up to about 40% of the total amount of the acrylic acid required), made by dissolving acrylic acid in the above solvent which also includes the free radical catalyst. The reaction zone is thereafter heated to a temperature within the range of from about 50°C to about 80°C and the remainder of the acrylic acid solution is added continuously to the reaction zone during the course of the reaction. The polymer is thereafter recovered from the reaction zone.

The poly(alkylene oxide) which can be crosslinked according to this invention includes a wide variety of known poly(alkylene oxides). It is believed that any poly(alkylene oxide) with a hydrogen atom on the carbon atom adjacent to the ether oxygen can be cross-linked as disclosed herein. Among the poly(alkylene oxides) which can be cross-linked according to this invention include homopolymers of ethylene oxide, propylene oxide and butylene oxide, copolymers of ethylene oxide, propylene oxide, butylene oxide and mixtures thereof. In general, poly(alkylene oxides) having an average molecular weight of at least 100,000 to about 5,000,000 or greater, up to 10,000,000 are operable. This invention is particularly adapted to the chemical cross-linking of poly(ethylene oxide) having a molecular weight of at least 100,000 which results in cross-linked products having a high degree of water absorption qualities, but is in no way, restricted thereto.

The relative amounts of poly(ethylene oxide) and acrylic acid employed in the process of this invention can also be varied over a wide range. In general, the amount of acrylic acid required is from about 1 – 50 percent by weight based on the amount of poly(ethylene oxide) used, and more preferably at a range from 6 – 30 percent of poly(ethylene oxide) used. This will give an end product with the best compromise of percent of crosslinked poly(ethylene oxide) content (i.e., water insoluble but swellable fraction) and water pickup ability (swellability) required when used in applications such as babies' diapers. However, it should be noted that concentrations outside the above range can also be used when products with either lower cross-linked poly(ethylene oxide) content but higher swellability or with higher cross-linked poly(ethylene oxide) content but lower swellability are desired.

A number of different free radical catalysts can be used in the process of this invention. Typical free radical catalysts include: azobisisobutyronitrile, benzoyl peroxide, acetyl peroxide, and 2,4-dichlorobenzoyl peroxide and, in general, any free radical generating compound which will generate a substantial number of free radicals over a temperature range of interest from about 50°C to about 100°C. The preferred free radical initiator for acrylic acid cross-linked poly(ethylene oxide) is acetyl peroxide. The amount of catalyst may vary from 0.005 – 2.5 (by weight) percent based on amount of poly(ethylene oxide), more preferably 0.01 – 1.5 percent. Again the acetyl peroxide or other initiator can also be used in a concentration outside the above cited limit, but the product obtained would have higher content of uncross-linked or soluble poly(ethylene oxide).

The duration of addition of acrylic acid is not critical since, as is known to those skilled in the art, it will vary according to the size of the batch, the catalyst, the temperature and other variables. However, it is critical that at least a major amount of the total amount of the acrylic acid used be continually added to the reaction mixture containing the poly(ethylene oxide), the solvent and catalyst in the reaction zone. As previously indicated, a minor amount of the acrylic acid can initially be present in the reaction zone with the poly(ethylene oxide), the solvent and the catalyst.

The temperature and reaction time at which the process can be carried out is related to the particular catalyst used in the reaction. The temperature range for cross-linking poly(ethylene oxide) can be varied from about 40°C to about 100°C and the time for the reaction can be from about 24 hours to half an hour. The preferred temperature is from about 50° to about 80°C, and the time for the complete reaction from about 3 to 5 hours, particularly when using acetyl peroxide as catalyst.

Another important criterion for the successful practice of the invention is the employment of a solvent for or during the cross-linking reaction. Liquid organic hydrocarbon solvents, which are inert to the reaction, can be utilized. A free flowing powdery product is obtained when an aliphatic and acyclic hydrocarbon such as hexane, heptane and cyclohexane are used. Viscous, gel-like product is obtained when an aromatic solvent such as benzene is used. Mixtures of aliphatic and aromatic solvents can also be used. Depending upon the ratio of the two solvents cross-linked products ranging from free flowing powder to viscous gel can be made. It is preferred to use a mixed solvent wherein the aliphatic hydrocarbon component is 50 percent or more (by volume) so that the cross-linked product can still remain as a free flowing powder throughout the whole reaction but with maximum water pickup ability (or swellability).

The ratio of solvent to poly(ethylene oxide) can be varied over a wide range. As a general rule, the ratio of solvent/poly(ethylene oxide) can be within the range of about 3 – 10 to 1 and more preferably within a range of about 4 – 8 to 1.

The following examples will more fully illustrate the process and cross-linked polymers of this invention.

Example I

A mixed solvent was prepared by mixing 500 ml of heptane and 380 ml benzene. Into a 1 liter, 4-neck round bottom flask fitted with a mechanical stirrer, a condenser, an addition funnel and a $N_2$ inlet and outlet were added 400 ml of the above mixed solvent, 60 grams of poly(ethylene oxide) having a molecular weight of about 5,000,000, 100 ml of an acrylic acid solution made by dissolving 6 grams of acrylic acid in 300 ml of the mixed solvent described above and 0.036 g. of acetyl peroxide. The ingredients were added under nitrogen. The reaction flask was heated in a constant temperature bath at 73°C. The remainder of the acrylic acid solution, i.e. 200 ml, was placed in the addition funnel and dropped into the reaction mixture in such a way that the addition lasted for 3.5 to 4 hours. After the addition the mixture was heated for another half hour, and the polymer was filtered and dried. The yield was 100 percent.

One gram of the recovered polymer was weighed and immersed in 100 ml of distilled water. The weight of the swollen polymer gel was 34 grams (swellability = 34) and the soluble percent of polymer (uncross-linked fraction) was 18.8 percent. When the polymer was partially (~50 percent neutralized) converted to its Na-salt with methanolic-MeONa, the Na-salt of the polymer showed a swellability of 41.2 and solubles of 20 percent. The pH of the swollen polymer gel was 5.5.

Example II

The apparatus utilized and the procedure of Example I was followed except that 0.25 g. of acetyl peroxide was added under nitrogen.

When the recovered polymer was partially (~50 percent neutralized) converted to its sodium salt with methanolic-MeONa, the sodium salt of the polymer showed a swellability of 48.6 and solubles of 24.9 percent. The pH of the swollen gel was 5.90.

Example III

The apparatus utilized and the procedure of Example I was followed except that the carboxyl group on the polymer was completely neutralized with methanolic-MeONa. The sodium salt of the polymer showed a swellability of 40.6 and solubles of 24 percent. The pH of the swollen gel was 8.42.

Example IV

The apparatus utilized and the procedure of Example I was followed except that 12 grams of acrylic acid were used.

The recovered polymer was not neutralized and was tested for swellability and solubles content. The polymer showed a swellability of 26.6 and solubles of 14.9 percent. The pH of the swollen gel was 3.52.

Example V

The apparatus utilized and the procedure of Example I was followed except that 0.30 g. of acetyl peroxide was added under nitrogen.

When the recovered polymer was partially (~60 percent neutralized) converted to its ammonium salt with ammonium hydroxide, the ammonium salt of the polymer showed a swellability of 42.8 and solubles of 19.5 percent. The pH of the swollen gel was 5.97. The unneutralized polymer had a swellability of 31.5 and solubles of 21.5 percent. The pH of the swollen gel was 3.83.

Example VI

The apparatus and procedure of Example I was followed except that 15 grams of poly(ethylene oxide) and 2.0 grams of acrylic acid were used. The acrylic acid was dissolved in 50 ml of the solvent and 10 ml of the solution was added to the reaction mixture at the beginning of the reaction together with poly(ethylene oxide). The remainder of the acrylic acid solution, i.e. 40 ml, was dropped in slowly during the reaction. The acetyl peroxide used was 0.07 grams. The acid form of the resultant polymer had a swellability of 21.7 and solubles of 15 percent. The swellability of the Na-salt of the polymer was 48 and the solubles 14.8 percent.

Example VII

The apparatus and procedure of Example VI was followed except that poly(ethylene oxide) was not present when acrylic acid was dropped in, but added at the end of the reaction. The polymer recovered was completely soluble in water.

The following examples show the swellability and solubles of acrylic acid treated poly(ethylene oxide) when various methods of addition of acrylic acid are employed. The procedure and apparatus of Example I were utilized except as otherwise indicated and the manner of addition of acrylic acid was as indicated in Table I. The recovered polymer was tested for swellability and solubles without neutralization. The results are indicated in Table I.

TABLE I

SWELLABILITY AND SOLUBLES OF ACRYLIC ACID TREATED POLYOX

| Example No. | Weight Percent Acrylic Acid | Method of Addition of Acrylic Acid | Swellability | Solubles |
|---|---|---|---|---|
| 8 | 10 | All at the beginning of the reaction. | 38 | 42.8 |
| 9 | 10 | Two increments, 1.5 hrs. apart. | 32.3 | 32.3 |
| 10 | 10 | Three increments, each 1.0 hour apart. | 31.2 | 28.4 |
| 11 | 13.3 | Dropped in slowly throughout the whole reaction. | 21.7 | 15.2 |
| 12 | 13.3 | Dropped in slowly throughout the whole reaction, but POLYOX was added after the addition of the acrylic acid instead of being present in the mixture during the addition. | Soluble | — |

As is demonstrated by the foregoing examples, gradual addition of acrylic acid to a slurry of poly(ethylene oxide) in a hydrocarbon solvent containing acetyl peroxide gives a water swellable product. The acrylic acid-cross-linked product contains free carboxyl groups which can be neutralized to alkali metal salts having even higher swellabilities than the acid form. No water swellable product is produced when poly(ethylene oxide) is added at the end of the reaction.

The easier wetting, faster swelling properties of the products of the present invention relative to cross-linked poly(ethylene oxide) produced by most other techniques are of significant value in uses such as in a disposable diaper. The presence of free carboxy groups also opens up a number of other applications. By adjusting the degree of neutralization a swellable polymer can be obtained with a desired pH to suit one's particular uses. For instance, when the polymer is partially neutralized to a pH of 5.5 – 6.0, it would be particularly suitable for those applications such as baby diapers, where the swollen gels might either directly or indirectly have contact with the skin, since the pH of a normal skin is about 5.5 – 6.0. Furthermore, since the carboxyl groups can be neutralized with various inorganic bases such as NaOH, KOH, $NH_4OH$, $Ca(OH)_2$ and $Mg(OH)_2$ as well as organic bases such as amines, the salt of the acrylic acid cross-linked poly(ethylene oxide) is also suitable as agricultural hydrogels. When applied to soil, the polymer not only helps to retain the moisture in the soil, it can also introduce elements such as N, K, and Ca to the plant when the acrylic acid treated poly(ethylene oxide) is neutralized with the desired base. Furthermore, because no hydrolysable linkages are used, the product would be more stable than the di-acrylate or the bis-acrylamide cross-linked product. The product is also more suitable for use as an acid or base thickening agent than conventionally cross-linked polymers.

What is claimed is:

1. A process for producing water swellable poly(alkylene oxide) which comprises introducing into a reaction zone an admixture of poly(alkylene oxide), having a molecular weight of at least 100,000 and an inert hydrocarbon solvent containing a free radical catalyst; adding to said reaction zone from 1% to 50% of acrylic acid, based on the weight of poly(alkylene oxide), the major portion to be added continuously, heating said reaction zone at a temperature within the range of 40°C to about 100°C for a time sufficient to produce said water swellable poly(alkylene oxide), and thereafter recovering said water swellable poly(alkylene oxide) from said reaction zone.

2. A process according to claim 1 wherein said poly(alkylene oxide) is poly(ethylene oxide).

3. A process according to claim 2 wherein a minor amount of acrylic acid is present in said reaction zone with said poly(ethylene oxide), solvent and catalyst and wherein the balance of acrylic acid used is continually added to the reaction mixture containing said poly(ethylene oxide), solvent, catalyst and minor amount of acrylic acid.

4. A process according to claim 3 wherein said inert hydrocarbon solvent is an aliphatic hydrocarbon solvent.

5. A process according to claim 3 wherein said free radical catalyst is acetyl peroxide.

6. A process according to claim 3 wherein the temperature maintained within the reaction zone is within the range of about 50°C to about 80°C.

7. A process according to claim 2 including the additional step of partially neutralizing said water swellable poly(ethylene oxide).

8. A product prepared by the process according to claim 7 wherein the resultant pH of said partially neutralized water swellable poly(ethylene oxide) is within the range of about 5.5 to about 6.0.

* * * * *